United States Patent [19]

Tongue

[11] Patent Number: 4,522,201
[45] Date of Patent: Jun. 11, 1985

[54] ORTHOPEDIC SURGERY DRILL GUIDE APPARATUS

[76] Inventor: John R. Tongue, 111 "C" Ave., Lake Oswego, Oreg. 97043

[21] Appl. No.: 485,047

[22] Filed: Apr. 14, 1983

[51] Int. Cl.$^3$ ............................................... A61F 5/04
[52] U.S. Cl. .............................. 128/92 EB; 128/92 E; 128/92 BA
[58] Field of Search ............. 128/92 R, 92 E, 92 EB, 128/92 A, 303 R, 92 BA, 92 BB

[56] References Cited

U.S. PATENT DOCUMENTS

| | | | |
|---|---|---|---|
| 2,200,120 | 5/1940 | Nauth | 128/92 EB |
| 2,607,339 | 8/1952 | Price | 128/92 EB |
| 3,704,707 | 12/1972 | Halloran | 128/92 EB |
| 3,765,034 | 10/1973 | Johnston | 128/92 EB |
| 4,360,012 | 11/1982 | McHarrie et al. | 128/92 EB |
| 4,383,527 | 5/1983 | Asnis et al. | 128/92 EB |

Primary Examiner—C. Fred Rosenbaum
Assistant Examiner—C. W. Shedd
Attorney, Agent, or Firm—Kolisch, Hartwell and Dickinson

[57] ABSTRACT

Orthopedic surgical guide apparatus for guiding the coaxial drilling of two different-diameter bores required for the insertion of repair hardware used in the mending of a broken bone. The apparatus includes a first, planar guide element which a surgeon uses throughout a procedure, and a second, generally cylindrical guide element employed during the first part of a procedure. The first guide element includes a large-diameter guide bore sized to guide a surgical reamer. The second guide element includes a body portion sized to fit removably in such larger-diameter guide bore, and also include a central, small-diameter guide bore which is coaxial with the large-diameter bore with the two guide elements assembled. The small-diameter guide bore is sized to guide a surgical guide pin (drill).

4 Claims, 13 Drawing Figures

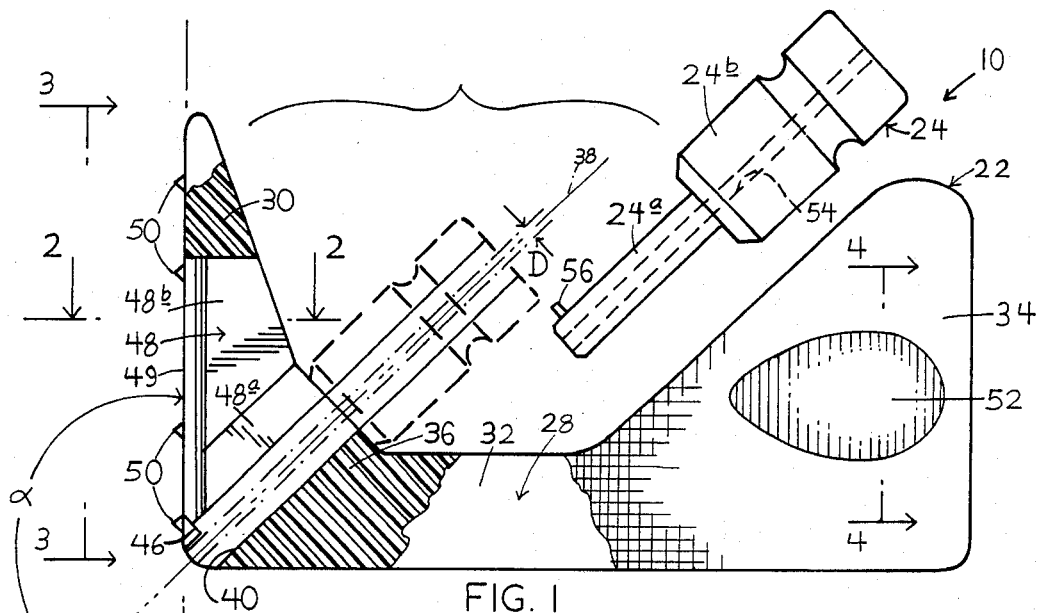
FIG. 1
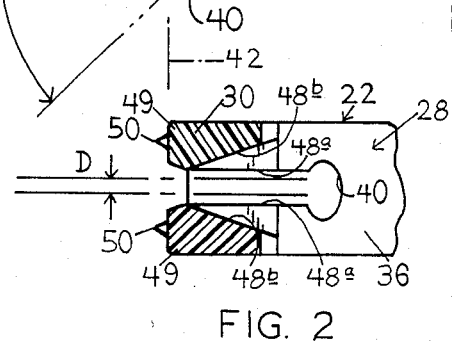
FIG. 2
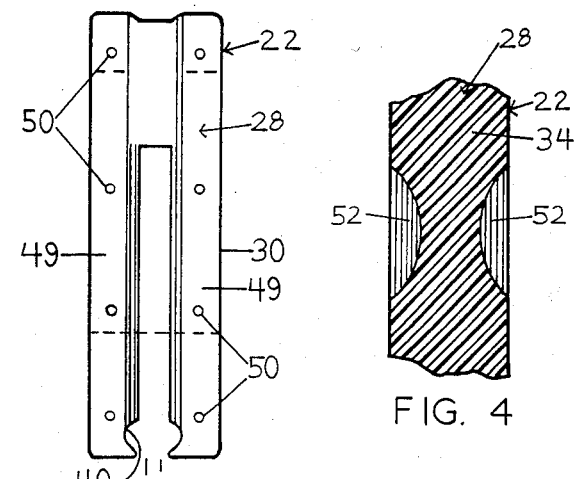
FIG. 4
FIG. 3
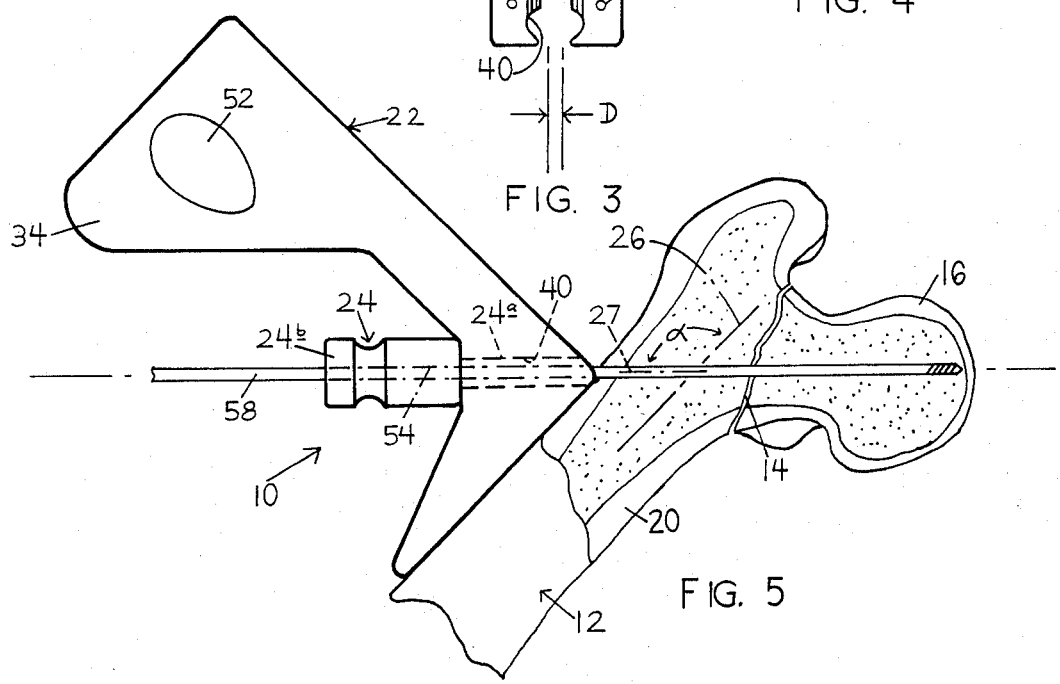
FIG. 5

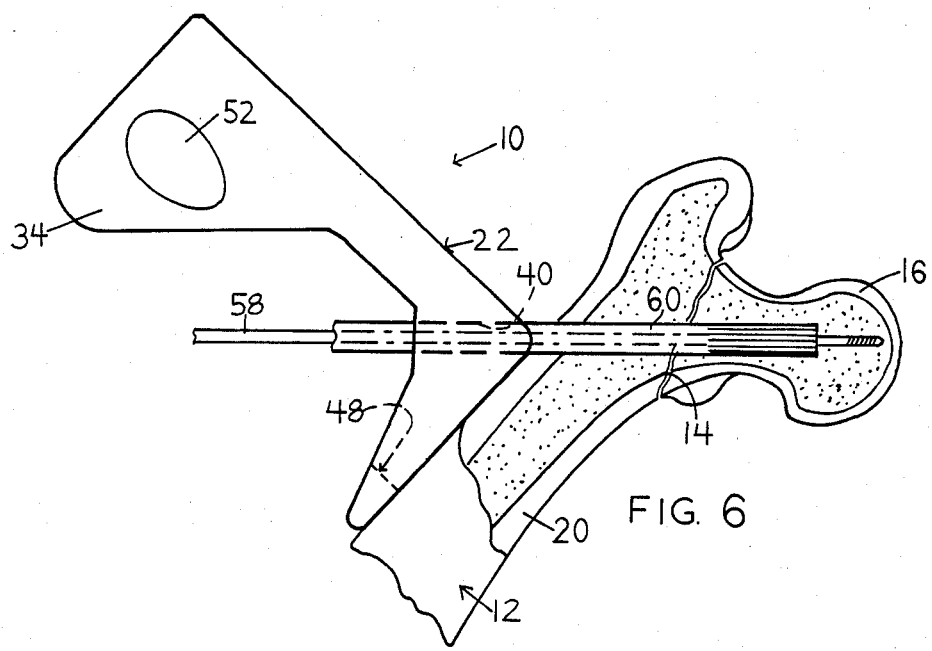
FIG. 6
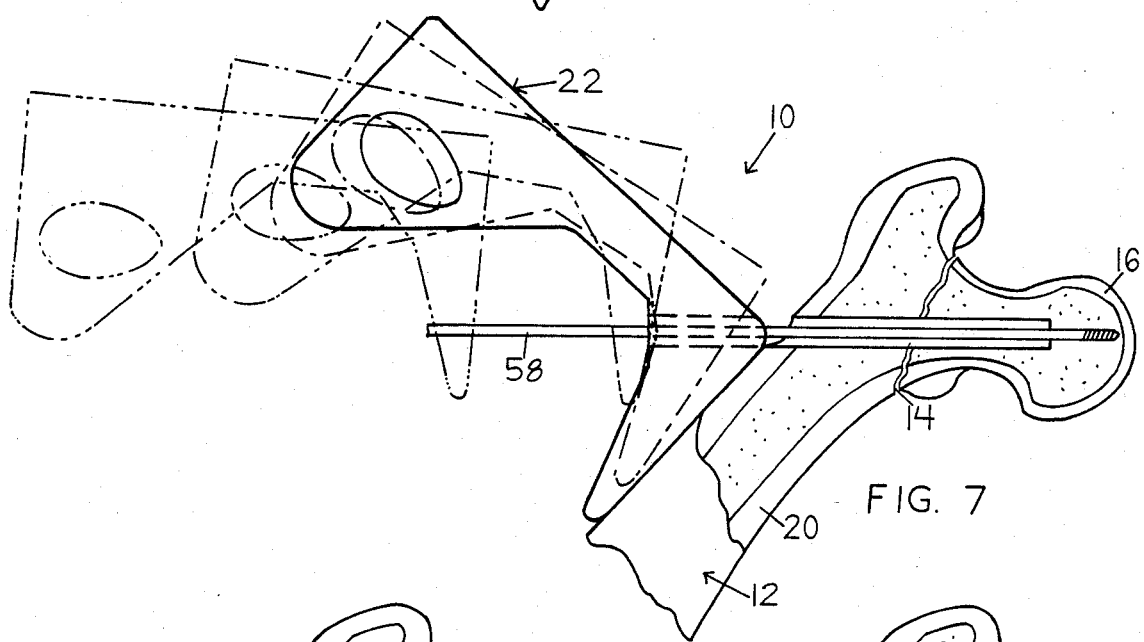
FIG. 7
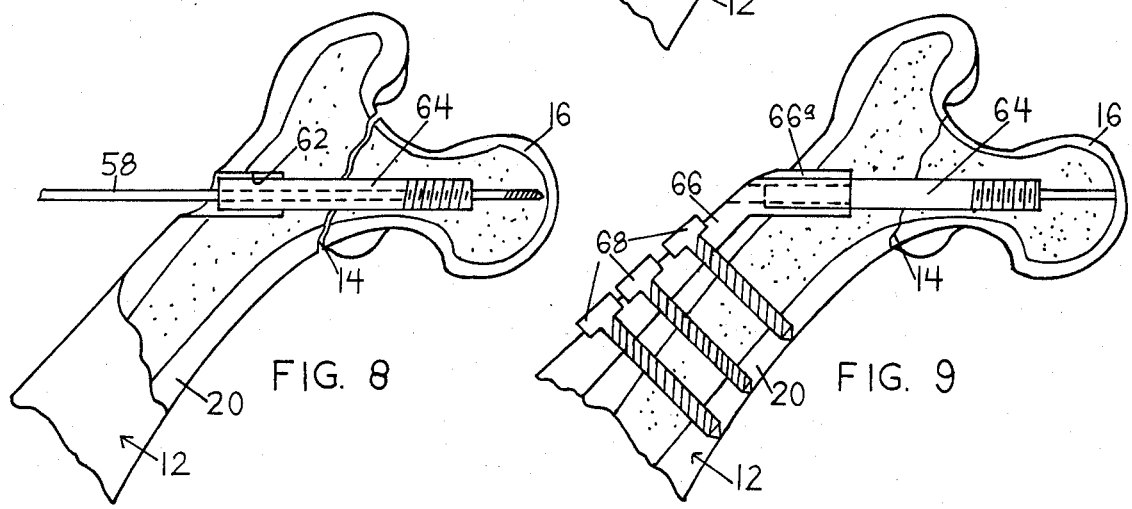
FIG. 8
FIG. 9

ORTHOPEDIC SURGERY DRILL GUIDE APPARATUS

BACKGROUND AND SUMMARY OF THE INVENTION

The present invention relates to a drilling guide for use in various orthopedic surgical procedures of the type requiring the drilling, along a common axis, of two different-diameter bores through a broken bone.

There are a number of orthopedic surgical procedures used in the repair of broken bones which require carefully controlled drilling, along a common axis, and at different times during the procedure, of two different-diameter bores which are required for the subsequent insertion of repair hardware. Among the procedures in which the invention finds particular utility are those known as open reduction internal fixation of a hip, osteotomy of the hip, osteotomy of the proximal tibia, and open reduction internal fixation of supra condylar fractures.

A preferred embodiment of the invention is described herein, for illustration purposes, in connection with open reduction internal fixation of the hip.

Conventional open reduction fixation of a hip fracture, such as a fracture at the base of the neck in the femoral head, involves the insertion of a surgical screw, and the attachment of a holding plate to the external surface of the bone. Preparation for the insertion of the screw requires, according to a procedure to be discussed herein, precision common-axis drilling of two bores having different diameters at a predetermined angle relative to the longitudinal axis of the bone. The procedure commences with the insertion (drilling in) of a slender guide pin at predetermined angle. The inserted guide pin projects from the lateral cortex of the femur, and continues through the femoral neck into the femoral head. The guide pin is then used to align coaxially a hollow-core reamer which forms a larger-diameter bore around the guide pin in preparation for the insertion of a surgical screw and plate. The reamer is then removed, and a hollow-core surgical screw is installed—guided by the guide pin. Thereafter, the guide pin is extracted, and a surgical fixation plate is attached which allows fracture compression, while maintaining alignment of the fracture during healing.

Guide pin and reamer alignment have been accomplished using a variety of methods and devices in the past. According to one method, the guide pin is inserted (drilled) using a "fixed-angle" drill guide which has a bore conforming to the outer diameter of the pin, and which, during the drilling process, is attached to the femur. Such a device provides angular alignment for the guide pin but is not usable thereafter for guiding a reamer.

Another procedure employs a drill guide having an adjustable-angle guide head. This kind of device, vis-a-vis drilling, works somewhat like a fixed-angle drill guide, with the main difference being that the guide head can be adjusted to permit drilling at different preselected angles, as dictated by the particular circumstance. However, problems have been encountered in the past where the angular position of the guide head slips during use.

A significant problem in the past has been that existing guides do not provide support for a reamer, which, accordingly, has been aligned solely by a guide pin. This situation frequently results in a bent guide pin, which does not provide proper guidance, and which, after bending, is caught inside the reamer, causing the guide pin to be directed through the hip joint into the pelvis, and then removed with the reamer leaving the fracture without support or landmarks.

A general object of the present invention, accordingly, is to provide a novel drill guide usable in orthopedic surgical procedures like those outlined above, specially designed to accomodate accurate, secure guidance for drills of two different diameters for coaxial drilling during such a procedure.

Another object is to provide such apparatus which is simple in construction, and easy, accurate, and "surefooted" during use.

According to a preferred embodiment of the invention, the same features a generally planar, somewhat C-shaped main guide body, or element, formed from a suitable plastic material which, conveniently, and to obtain an "in-use" advantage described below, may also be a radio-translucent material. The main guide body is formed with a non-slip handle which the physician may grip securely to position and manipulate the device adjacent a broken bone. An edge of this body opposite the handle is configured with a support surface for fitting snugly adjacent the femur during an operation, with pins projecting from this surface to furnish a high-friction, non-slip footing.

A bore of a predetermined angle (relative to the support surface) extends through the body, with the diameter of this bore being sized to furnish a clearance fit with a reamer of the type mentioned above.

A second, generally cylindrical, guide element, including a cylindrical body portion which fits within the bore of the first, or main, guide element, contains a second bore extending axially through the element. This bore has a smaller diameter than the first-mentioned bore, and specifically is sized to provide a clearance fit with a slender guide pin of the kind discussed earlier.

During a surgical procedure, with the main guide element placed and held against a femur, and with the second guide element assembled with the first element, the smaller-diameter bore just mentioned is used to guide the drilling insertion of a guide pin. The second guide element is thereafter removed by withdrawal along the axis of the guide pin, and the larger-diameter bore in the main guide element is then used to guide drilling of the reamer. After use of the reamer, the same is also withdrawn axially from the guide pin—supported during withdrawal by the bore wall in the first guide element, in a manner minimizing the likelihoood of bending the guide pin.

The main guide element is now removed from the surgical field, in either one of two different ways, according to the specific construction of "escape structure" provided according to two different modifications of the invention disclosed herein. According to one modification, the guide bore in the main guide element forms part of a specially shaped escape aperture. This aperture permits withdrawal of the first guide element by a first rotational movement in the plane of the element, to clear the support surface from any adjacent muscle tissue with which it may have become caught, followed by a second translational motion withdrawing it along the length of the guide pin. In a second modification of the invention, a lateral escape passage aperture is formed in the body of the first guide element, along one side of the guide bore therein, which passage permits withdrawal of the element by a first rotational movement generally normal to the plane of the element, to clear a guide pin from the guide bore, followed by a second rotational movement generally in the plane of the element to clear it from any adjacent tissue.

Various other features and advantages which are attained by the invention will become more fully apparent as the description that now follows is read in conjunction with the accompanying drawings.

DESCRIPTION OF THE DRAWINGS

FIG. 1 is a side elevation of one embodiment of orthopedic surgical drill guide apparatus constructed according to the invention, with two guide elements in the apparatus shown separated in solid outline, and with portions of what is referred to as the main guide element partially cut away to show details of construction.

FIG. 2 is a fragmentary section taken generally along the line 2—2 in FIG. 1.

FIG. 3 is a view taken generally along the line 3—3 in FIG. 1, depicting an end edge view of the main guide element.

FIG. 4 is a fragmentary section taken generally along the line 4—4 in FIG. 1.

FIG. 5 is a view showing the apparatus of FIGS. 1-4, and a guide pin, in place during an initial stage of an open reduction hip fixation procedure—soft tissue being omitted from the figure in order to simplify it.

FIG. 6 illustrates a later operational stage, and depicts use of the main guide element to guide a reamer.

FIG. 7 depicts a stage following that shown in FIG. 6, and shows progressive removal of the main guide element relative to the guide pin.

FIG. 8 illustrates a surgical screw inserted in the drilled bone, concentric with the guide pin.

FIG. 9 shows a hip fixation plate attached to the screw, completing the fixation procedure.

DETAILED DESCRIPTION OF THE INVENTION

Figure 10:
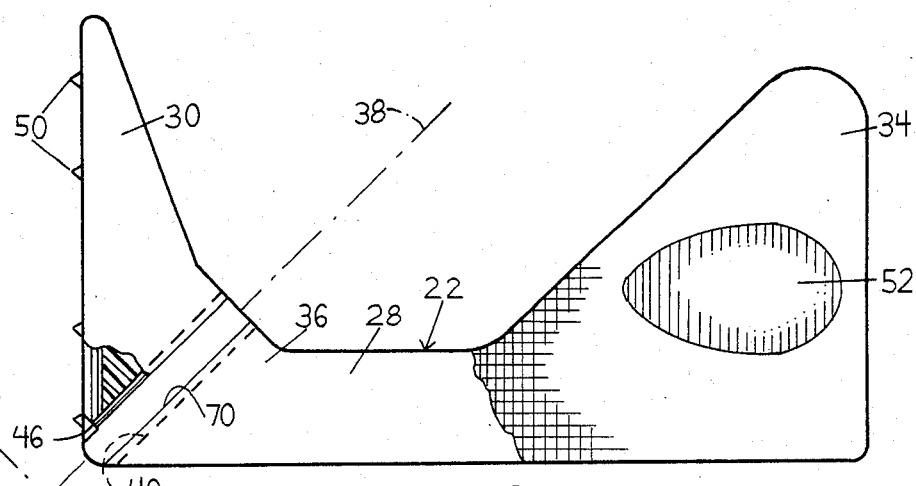
FIG. 10 is a side elevation, similar to FIG. 1, illustrating a modified form of a main guide element.

Turning now to the drawings, and referring first to FIG. 5, one embodiment of an orthopedic surgical drill guide apparatus constructed in accordance with the invention is shown generally at 10 positioned on a femur 12, which has a fracture 14 at the base of the neck of femoral head 16. The typical procedure for repair of such a fracture is referred to as an open reduction internal fixation of the hip—a procedure whereby the femoral head is fixed to the femoral shaft 20 by means of a conventional surgical screw and fixation plate.

Apparatus 10 features two separable parts, including what is referred to herein as a first, or main, guide element 22, and a second guide element 24. As has been outlined above, apparatus 10 is designed to provide accurate, secure guidance for drills of two different diameters which are used to drill successive coaxial bores required for proper reduction of the fracture in the femur.

Considering for a moment the geometry of the femur, as such relates to the fixation procedure herein to be described, what might be thought of as the longitudinal axis of the femur is shown at 26 in FIG. 5. Depending upon the specific location of a fracture, experience over the years has shown that common-axis drilling across the fracture, in order to provide appropriate hardware-accommodating bores, should take place at an angle $\alpha$ relative to the axis, which angle lies in the range from about 130° to about 150°. The fracture depicted in FIG. 5 is one which requires an $\alpha$ angle of 135° between axis 26 and a drilling axis 27. Accordingly, and as will be explained further, apparatus 10 is designed specifically to accommodate this angle. Obviously, simple modifications of the apparatus, which will be apparent to one skilled in the art based upon a reading of the disclosure herein, may be made to accommodate other specific desired drilling angles.

In an open reduction fixation procedure, not only is the drilling angle just described critical, so also are what might be thought of as the drilling "plane" relative to the common plane which contains the head and shank of the femur (the plane of FIG. 5), and the drilling position along the length of the femur. It is important that the surgeon control the drilling plane so as to prevent a drill in a procedure from cutting through the side of the head, and important to control the drilling position so that the chosen drilling angle assures that drilled bores extend substantially centrally through the femoral neck into the central core of the head.

As will be explained, guide element 22 is specially constructed with a planar configuration herein, including what is referred to as a web-like handle portion that enables the surgeon to "feel" easily how to hold the apparatus so as to assure a proper drilling plane. Attention to the question of controlling of drilling position depends upon attention to the fact that the environment in which such a procedure takes place is extremely slick and slippery. Here, as will be elaborated, guide element 22, on the edge thereof which is designed to seat against the femur during the procedure (as is shown in FIG. 5), is equipped with projecting pins that effect a high-friction, non-slip footing—preventing inadvertent slippage of the element relative to the femur.

Addressing attention now to FIGS. 1-4, inclusive, guide apparatus 10 is here shown in greater detail. Element 22 includes a generally planar web-like body 28, which, as seen from the point of view of FIG. 1, has the combined curved and angular, somewhat C-shaped outline seen in this figure. Body 28, which is formed preferably of a suitable radio-translucent plastic material such as a polyetherimide resin, includes what will be referred to herein as a head portion 30, a neck portion 32, and a handle portion 34. The head and neck portions are joined through what will be referred to herein as a bridging portion 36 which, in FIG. 1, extends upwardly and to the right in the body from the lower left corner thereof shown in the figure. The longitudinal axis of bridging portion 36 is shown at 38.

Provided in bridging portion 36, according to an important feature of the invention, is a bore 40, also referred to herein as a first guide bore, which opens to opposite extremities of the bridging portion as shown. Bore 40 is centered on axis 38 and has a selected diameter slightly greater than 5/16-inches, which is the diameter of a surgical reamer in conjunction with which apparatus 10 has been designed for use. In particular, bore 40 is sized for clearance fitment of such a reamer. Further considering axis 38 and bore 40, these are disposed at the same angle $\alpha$ mentioned in conjunction with FIG. 5, relative to the plane shown at 42 (FIG. 1)

which is substantially occupied by the left marginal edge of body 28 in FIG. 1, which edge is also referred to herein as a support surface in guide element 22.

Focusing attention on the lower left corner of body 28, adjacent the outer end thereof, bore 40 terminates in what may best be described as a semi-circular, stepped-up-diameter cut-away portion having a semi-annular shoulder 46 whose purpose will be explained shortly.

Formed above bore 40 in FIG. 1, and extending in the plane of FIG. 1 completely through head portion 30 (in a right/left sense) is a void region 48 which, together with the bore, forms what is referred to herein as an escape aperture. The lower portion of this void region is defined by parallel-planar walls 48a which are spaced apart, as can be seen particularly in FIG. 2, by a distance which is less than the diameter of bore 40. Also, this wall spacing, according to the invention, is somewhat greater than the diameter, shown at D in FIGS. 1, 2 and 3, of a slender guide pin in conjunction with which the apparatus is intended to be used. In the particular embodiment now being described, walls 48a are spaced apart by about 3/16-inches. Extending upwardly from walls 48a, and further defining void space 48, and flared walls 48b which define what is referred to as a flared portion of the aperture. Walls 48b diverge progressing from left-to-right as seen in FIGS. 1 and 2.

Referring back for a moment to that edge in body 28 which extends generally in previously mentioned plane 42, this edge is provided with a longitudinal central channel which defines a pair of substantially parallel, laterally spaced ribs 49. This configuration in the edge which is intended to be seated against a femur during an operation, enables element 22 to conform easily to radial curvature in the shaft of the femur. This same edge is also referred to herein as a generally planar support surface. Suitably embedded in the material forming head portion 30, and projecting as shown from ribs 49 are sharp-pointed pins, such as those shown at 50. These pins provide a secure, anti-slip, frictional footing against a femoral shaft during an operation.

Completing a description of element 22, opposite sides of handle portion 34 are knurled as shown, and are provided with thumb depressions 52. These features greatly facilitate gripping and manipulation of element 22 during an operation.

Addressing attention now to guide element 24, this element includes a small-diameter cylindrical body portion 24a which joins integrally with a larger-diameter cylindrical head portion 24b. The outside diameter of body portion 24a is sized for clearance fitment in bore 40, with portion 24a having an axial length which is roughly the same as that of bore 40. Extending axially centrally through element 24 is an elongated bore 54 which is sized for clearance fitment with a guide pin of the size intended for use with apparatus 10. In the particular case now being described, such a pin has a diameter of about ⅛-inches. Accordingly, bore 54 has a diameter just slightly larger than this dimension. Body portion 24a in element 24 is designed for removable reception within bore 40 in element 22, and when so received, aligns the axis of bore 54 substantially coaxially with that of previously mentioned axis 38. Element 24 herein is also made of a polyetherimide resin.

Projecting radially, as can be seen in FIG. 1, from the lower end of body portion 24a in the figure, is a locking pin 56 which is used as will be explained to prevent inadvertent withdrawal of element 24 from element 22 when the two elements are assembled.

Explaining now how apparatus 10 is used during an open reduction internal fixation of the hip bone shown in FIG. 5, guide element 24 is assembled with element 22 by inserting body portion 24a into bore 40, with pin 56 extending into that part of the keyway aperture defined between walls 48a. When, relative to element 22, element 24 reaches the position shown therefor in dashed lines in FIG. 1, the head portion of element 24 is twisted (clockwise or counterclockwise) so as to place pin 56 in a position away from the space between walls 48a, and confronting shoulder 46. Under such a circumstance, inadvertent axial withdrawal of element 24 from bore 40 is prevented.

With the two guide elements so assembled, the assembly is placed against femur 12 as shown in FIG. 5. Pins 50 seat on the side of the femoral shaft to prevent slippage of the apparatus. The handle portion in element 22 facilitates "planar" positioning of the apparatus as mentioned earlier.

With the apparatus so positioned, and employing conventional power-drive apparatus, a guide pin, such as the one shown fragmentarily at 58 in FIG. 5, is fed through bore 54 by means of which it is guided at the proper angle and disposition into the femur and across fracture 14 into head 16. The guide pin is driven substantially to the extended position relative to the femur shown in FIG. 5.

With the guide pin so inserted, the power-drive apparatus is removed therefrom, and guide element 24 is twisted and then extracted from further use along the length of the pin. Retraction and removal of element 24 exposes bore 40 for the reception of a reamer, and such a reamer, guided both by pin 58 and by bore 40, is now power-driven to drill into the femur and across the fracture into head 18, as shown for a reamer 60 in FIG. 6.

Following this operation, the reamer is withdrawn along the length of the guide pin, and guide element 22 now is removed from further use, in accordance with the description which will now follow in relation to FIG. 7.

Removal of guide element 22 begins with a slight rotation of the element, substantially within the plane of the element, to shift it successively from its solid outline position in FIG. 7 toward its dash-dot outline position in the figure, and thence toward its dash-double-dot outline position in the figure. This motion frees the head portion of the element from any snagging with adjacent muscle tissue, and is accommodated by the escape aperture which allows pin 58 to escape from the confines of bore 40. The flared portion in the aperture allows, where such is necessary, some up and down rocking of the element (relative to the plane of FIG. 7) further to facilitate separation from surrounding tissue.

With the element shifted substantially to the position shown for it in dash-double-dot lines in FIG. 7, complete removal of the element takes place by translational withdrawal thereof along the length of pin 58, as is indicated in the dash-triple-dot outline position shown in the figure.

What appears in FIGS. 8 and 9 generally completes the story relating to the installation of repair hardware. In FIG. 8, the lateral cortex of the femur is enlarged, as shown at 62, in a conventional manner and for a purpose shortly to be explained. Using the still-installed guide pin 58 which, throughout the procedure, remains in place to stabilize the fracture and to maintain the proper α angle, a conventional surgical repair screw 64 is threaded in place.

The guide pin is now removed, and a fixation plate 66, seen in FIG. 9, having a neck portion 66a received in bore enlargement 62, is fastened to screw 64 conventionally, and is secured to the shaft of femur 12 by means of screws, such as those shown at 68.

The advantages thus offered by apparatus 10 should be apparent. The apparatus provides for precision, supported guidance for placement and use of guide pin 58 and reamer 60. Guide element 22 is easily manipulated by a surgeon to assure proper directing of these two drill units, vis-a-vis both the position of drilling, and the "plane" of drilling. The preset angle between the axis of bore 40 and plane 42 assures precise angular location for the coaxial drilled bores. With guide element 24 operable with element 22 in the manner described, and with element 22 including the aperture escape structure described, use and removal of the guide apparatus is accomplished easily with little likelihood of guide-pin bending.

Radio translucence in the material forming guide elements 22, 24 facilitates X-ray monitoring of the positions of a guide pin and a reamer during a procedure.

Figure 11:
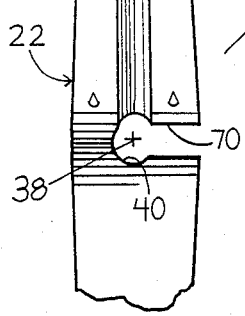
FIG. 11 is a fragmentary view taken generally along the line 11—11 in FIG. 10.

FIGS. 10 and 11 disclose a modified form of guide element 22, which differs from that shown in FIGS. 1-4 substantially only with respect to escape aperture structure provided for clearing a guide pin, such as pin 58, from bore 40. Accordingly, absent from guide element 22 shown in FIGS. 10 and 11 is an aperture like that previously described, and in its place is an elongated passage 70 which extends along the length of bore 40. In FIG. 10, bore 70 is on the side thereof which faces the viewer, and in FIG. 11 is on the right side of the figure. Passage 70 has a lateral width which is substantially the same as the spacing described earlier between walls 48a.

Figure 12:
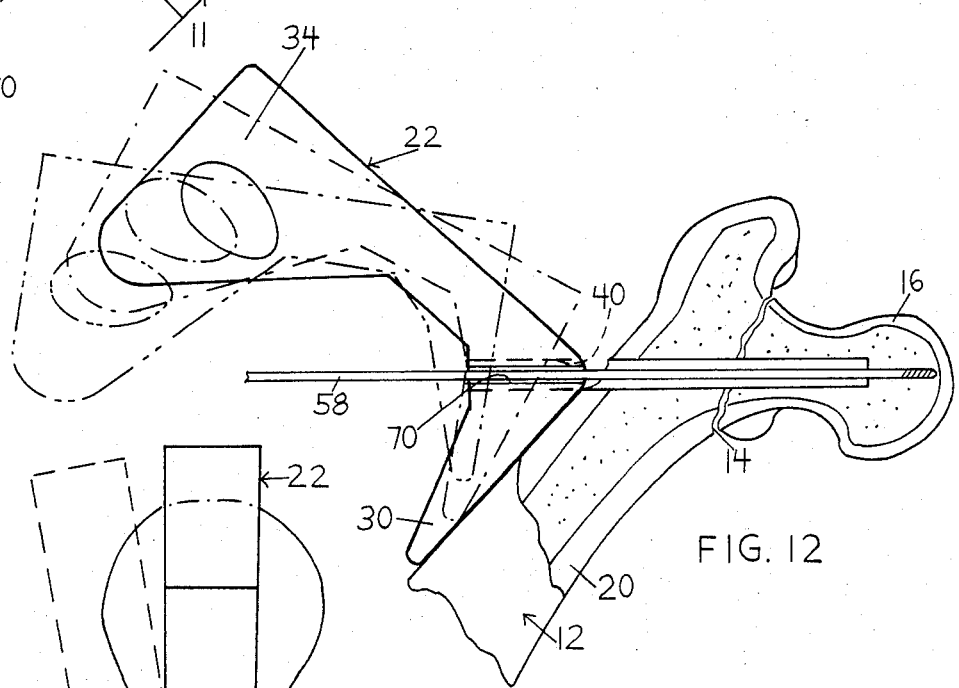
FIGS. 12 and 13 illustrate progressive removal of the modified guide element of FIG. 10 relative to a guide pin.

When using this modification of the invention, all of the steps of an open reduction internal hip fixation, up to the step of removing element 22 from the scene, are substantially the same. FIG. 12 is similar to FIG. 7 in the sense that it illustrates, in solid lines, the relative condition existing between element 22 and femur 12 just prior to the element's removal.

Figure 13:
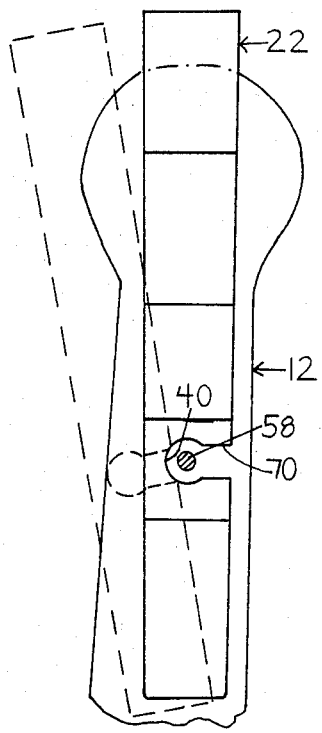

According to this modification of the invention, removal of element 22 begins with a slight rotation of the element, depicted in FIG. 13, in a direction which is generaly normal to the plane of the element. In solid lines in FIG. 13, element 22 and femur 12 are shown in the same relative positions also depicted in solid lines in FIG. 12. The rotation just described takes place counterclockwise in FIG. 13 to shift element 22 toward its dashed-line position in the figure. As can be seen, this slight cross-plane rotation permits guide pin 58 to escape from bore 40 through lateral passage 70. Thereafter, complete removal of element 22 takes place as is depicted in FIG. 12, with slight rotation of the element generally in its plane from the solid outline position shown for the element, toward the dash-dot outline position, and thence toward the dash-double-dot position shown for the element. This final motion frees head portion 30 from any entrapping tissue, and obviously is accomplished without any likelihood of guide pin bending, inasmuch as the guide pin is now completely free from element 22.

It should be apparent, therefore, how both modifications of the invention described herein offer all of the features and advantages ascribed to the invention earlier herein. While a preferred embodiment, and a modification, of the invention, have been shown and described, it is appreciated that other variations and modifications may be made without departing from the spirit of the invention.

It is claimed and desired to secure by Letters Patent:

1. Orthopedic surgical guide apparatus for use in the preparation of a fractured bone, such as a hip bone, in an orthopedic procedure requiring the drilling along a common axis of two different-diameter bores in such a bone, said apparatus comprising a first guide element having means defining a generally planar support surface for seating against such a bone, and means defining a first guide bore which opens to said surface with an axis disposed at a predetermined angle relative to the plane of said support surface for receiving and clearance-guiding a drill having a diameter equaling the larger of such two different diameters, and a second guide element having an elongate cylindrical body portion removably-clearance-fittable within said first guide bore, and a second guide bore extending axially centrally through said body portion for receiving and clearance-guiding a drill having a diameter equaling the smaller of such two different diameters, said first guide element further including a drill escape aperture communicating with and extending laterally relative to the axis of said first guide bore.

2. The apparatus of claim 1, wherein said first guide element includes a web-like manipulation handle portion.

3. The apparatus of claim 1, wherein said escape aperture takes the form of an elongate passage which exposes the length of said first guide bore along one side of the first guide element, said passage, when viewed along a line normal to said axis, having a width less than the larger of such two diameters and greater than the smaller of such two diameters, and accommodating with said first guide element in place relative to a bone, with a drill of such smaller diameter embedded in the bone, and with said second guide element removed, withdrawal of the first guide element relative to such drill through rotation and retraction of the first guide element laterally away from said axis.

4. The apparatus of claim 1, wherein said escape aperture exposes the length of said first guide bore at the location substantially of said support surface, which aperture, with said first guide element in place relative to a bone, with a drill of such smaller diameter embedded in the bone, and with said second guide element removed, accommodates clearance removal of the first guide element relative to such drill through rotation and retraction of the first guide element generally in a direction normal to the plane of said support surface.

* * * * *